US00PP32990P2

(12) United States Plant Patent
Hansen

(10) Patent No.: US PP32,990 P2
(45) Date of Patent: Apr. 20, 2021

(54) ***PHLOX* PLANT NAMED 'CRATER LAKE'**

(50) Latin Name: ***Phlox* hybrid**
Varietal Denomination: Crater Lake

(71) Applicant: Hans A Hansen, Zeeland, MI (US)

(72) Inventor: Hans A Hansen, Zeeland, MI (US)

( * ) Notice: Subject to any disclaimer, the term of this patent is extended or adjusted under 35 U.S.C. 154(b) by 0 days.

(21) Appl. No.: 16/974,099

(22) Filed: Sep. 30, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A unique cultivar of Hybrid Creeping *Phlox* named 'Crater Lake' characterized by vigorous, dense, spreading, multi-stemmed, winter-hardy habit with short, bright green, linear to awl-shaped leaves. Flowering begins in late-April and continuing for up to six weeks, in cooler weather conditions, on heavily-branched peduncles and completely cover the plant in peak season. Petals of newly opened flowers are cool indigo-purple with a small notch and the tips of the petals. The new plant is able to withstand dry conditions once established, and the foliage stays clean and resists mildew. The new plant is especially suitable for the landscape as a potted plant and in the garden as a specimen or en masse.

1. Vigorous plants of dense, slowly-spreading habit, spreading by rooting stems, producing short, clean, glabrous, bright-green, narrow leaves;
2. Multiple heavily-branched stems produce branched panicles;
3. Flower beginning in late-April and continuing for up to six weeks, in cool conditions, completely covering plant at peak flowering;
4. Flowers of cool indigo-purple and with small notches at the tip of the petals;
5. Plant is able to withstand dry conditions once established.

1 Drawing Sheet

Botanical classification: *Phlox* hybrid.
Variety denomination: 'Crater Lake'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. on Feb. 2, 2020. Subsequently, the new plant was advertised in the "Walters Gardens 20-21 Catalog" by Walters Gardens, Inc. released on May 20, 2020. The claimed plant was first sold to the public on Mar. 16, 2020 by Walters Gardens, Inc., who obtained the plant and all information relating thereto, from the inventor. No plants of *Phlox* 'Crater Lake' have been sold to the public in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hybrid Creeping *Phlox* plant known as *Phlox* 'Crater Lake' and will be referred to hereafter by its cultivar name, 'Crater Lake', or the "new plant". The new plant was hybridized by the inventor at a wholesale perennial nursery in Zeeland, Mich. on May 1, 2015 as a cross between *Phlox subulata* 'Purple Beauty' (not patented) as the female or seed parent and *Phlox kelseyi* 'Lemhi Purple' (not patented) as the male or pollen parent. The new plant passed initial evaluation on the spring of 2018 and was assigned the breeder code 15-42-2 through the remaining evaluation process. 'Crater Lake' was first asexually propagated by stem cuttings in the greenhouses at the same nursery in Zeeland, Mich. in the summer of 2018. The unique characteristics of the new plant have been found to be reproducible and stable in successive generations of asexually propagated and the resultant plants have been found to be identical to the original selection.

BRIEF SUMMARY OF THE PLANT

*Phlox* 'Crater Lake' is unique from all other Hybrid Spring *Phlox* known to the inventor. The nearest comparison plants known to the inventor include: 'Rocky Road Grape' U.S. Plant Pat. No. 32,248, 'Rocky Road Violet Blue' U.S. Plant Pat. No. 32,288, 'Violet Pinwheels' U.S. Plant Pat. No. 25,884, 'Rocky Road Periwinkle' U.S. Plant Pat. No. 32,325 and 'Plumtastic' U.S. Plant Pat. No. 28,896. 'Rocky Road Grape' has flowers that are red-purple with larger notched apices. 'Rocky Road Violet Blue', a sister seedling to the new plant, has flowers of violet-blue with dark pink eye and with small notches at the tip of the petals. 'Violet Pinwheels' has slightly shorter height with violet-blue flower color with more cupped corolla and more deeply cleft petal apices and narrower petals. 'Rocky Road Periwinkle' has periwinkle-blue flowers. 'Plumtastic' has flowers of violet-pink with purple markings near the eye, and the flower initially has a light, near-white center that darkens to the same violet-pink at maturity.

The female parent, 'Purple Beauty', has purple flowers with deeper cleft petal apices and the habit is taller and more vigorously spreading. The male parent, 'Lemhi Purple', has flowers that are fade more from a deep lavender to a lighter pinkish-blue and the habit is much shorter and less broadly spreading.

*Phlox* 'Crater Lake' differs from and all other *Phlox* known to the inventor in the following repeatedly observed traits in combination:

1. Vigorous plants of dense, slowly-spreading habit, spreading by rooting stems, producing short, clean, glabrous, bright-green, narrow leaves;
2. Multiple heavily-branched stems produce branched panicles;
3. Flower beginning in late-April and continuing for up to six weeks, in cool conditions, completely covering plant at peak flowering;
4. Flowers of cool indigo-purple and with small notches at the tip of the petals;
5. Plant is able to withstand dry conditions once established.

BRIEF DESCRIPTION OF THE DRAWINGS

The photographs of the new plant demonstrate the unique traits of *Phlox* 'Crater Lake' and the overall appearance of the plant at three-years-old growing in a full-sun trial beds in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
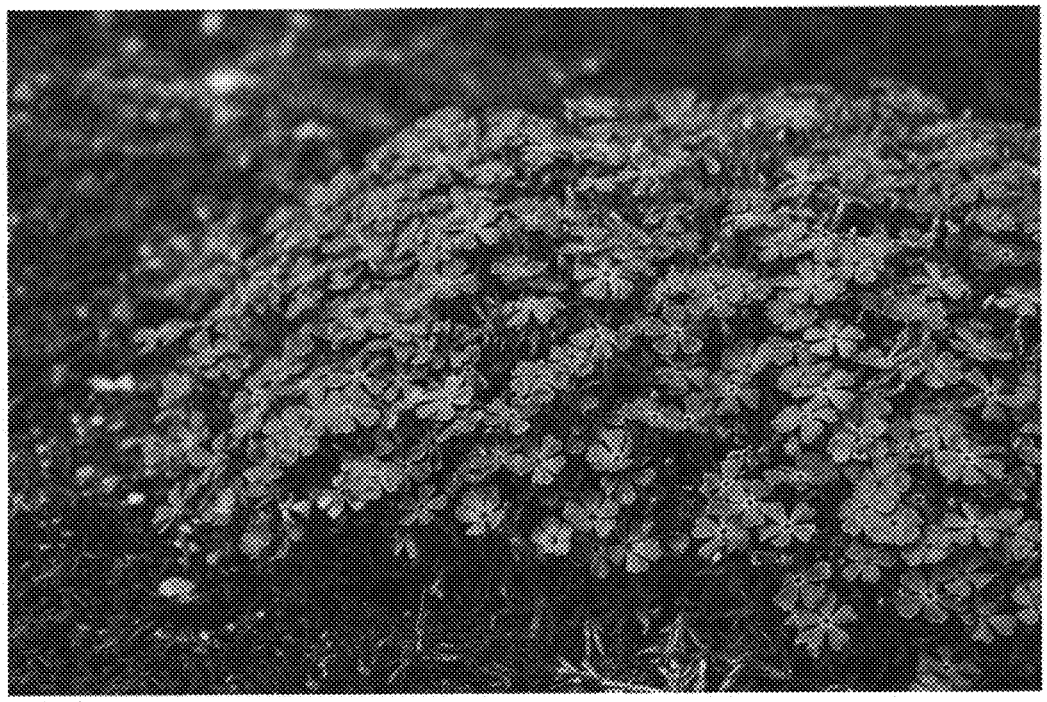
FIG. 1 shows a landscape habit view of the new plant in peak flower.
Figure 2:
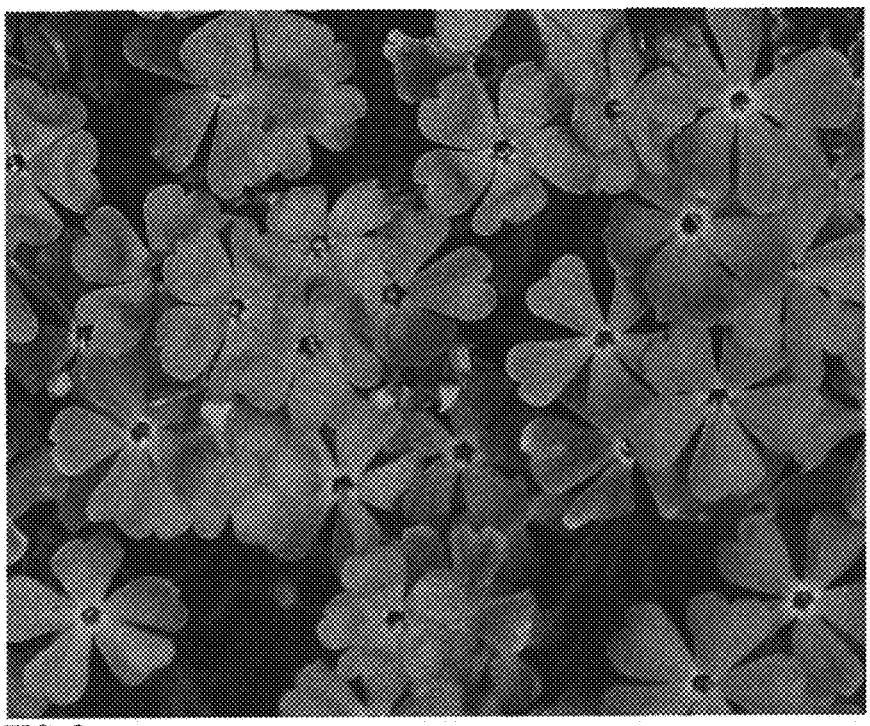
FIG. 2 shows a close-up of the flowers and buds.

The following descriptions and color references are based on the 2015 edition of The Royal Horticultural Society Colour Chart except where common dictionary terms are used. *Phlox* 'Crater Lake' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox* hybrid;

Parentage: Female or seed parent is *Phlox subulata* 'Purple Beauty', male or pollen parent is *Phlox kelseyi* 'Lemhi Purple';

Plant habit: Winter-hardy, evergreen herbaceous perennial; short, dense, producing about 60 to 80 stiff, highly-branched prostrate stems; foliage to 13.5 cm tall and 70.0 cm wide, average 13.0 cm tall and 66.0 cm wide; flowering to 13.0 cm tall and 74.0 cm wide;

Propagation: Stem cuttings; rooting in about 3 weeks;

Time to produce finished crop in 3.8 liter pots: About 8 to 12 weeks; moderately vigorous;

Root: Fibrous and freely branching; color creamy white to tan depending on soil type;

Leaves: Simple; opposite proximally, whorled distally; linear to subulate; apex narrowly acute to mucronulate; base truncate, clasping; margin entire and micro-ciliolate; glabrous and matte both adaxial and abaxial; about 20.0 mm long by about 2.0 mm wide at base, average about 16.0 mm long and 2.0 mm wide;

Leaf color: Adaxial expanding and mature nearest RHS 137B, abaxial both expanding and mature nearest RHS 138A;

Foliage fragrance: None detected;

Veins: Pinnate; not conspicuous adaxial and abaxial;

Vein color: Same color as surround leaf;

Petiole: Leaves sessile;

Stems: Cylindrical; flexible; wiry; prostrate; highly branching; to about 15.0 cm long and 1.0 mm diameter near base;

Stem color: Color nearest RHS NN155A when exposed;

Nodes: Proximally about 3.0 mm apart; distally less than 1.0 mm apart;

Node color: Color between RHS NN155A and RHS 196D;

Inflorescence: Upright to outwardly; about 2.5 cm long and 3.0 cm wide; average of 3 flowers;

Flowers: Perfect; salverform; mostly flat faced; about 21.0 mm across face and 16.0 mm long; with fused corolla tube about 14.0 mm long and 2.5 mm diameter near face; attitude upright to outwardly;

Flower longevity: About 5 days on plant; self-cleaning;

Flower fragrance: Not detected;

Buds one to two days prior to opening: Narrowly oblanceolate, to narrowly clavate; bluntly acute apex with rounded base; petals implicate; about 18.0 mm long, 7.0 mm long in terminal bulb portion and 11.0 mm long in tube; corolla tube to 2.0 mm diameter, bulb to 3.5 mm diameter;

Bud color: Exposed petal bulb portion nearest RHS 85C; ring between tube and bulb nearest RHS N92A, corolla tube basal 2.0 mm nearest RHS 145C and distal tube nearest RHS 86C; calyx nearest RHS 147B with slight blush in high light exposure of nearest RHS N187A;

Petals: Five; obtuse; consisting of limb and basal claw fused into corolla tube; apex rounded, crenulate and shallowly emarginate, cleft to about 0.5 mm deep; limbs not imbricate; margin entire; glabrous adaxial and abaxial;

Petal size: Limb about 9.5 mm long and 8.0 mm wide near middle; tube about 14.0 mm long and 2.0 mm diameter;

Petal color upon opening:

*Adaxial.*—Limb nearest RHS N81C with two faint splashed dots near eye about 0.5 mm long and wide nearest RHS 93A; proximal 4.0 mm of tube nearest RHS 145C, remaining distal tube portion nearest RHS 85B.

*Abaxial.*—Limb between RHS N82C and RHS N82D, proximal 1.0 mm of tube nearest RHS 145B, next proximal 2.0 mm nearest RHS 150D, remaining distal tube portion nearest RHS 86D.

Petal color upon maturity:

*Adaxial.*—Limb between RHS N81C and RHS N81A with a ring near center between RHS N155A and RHS NN155D, proximal 4.0 mm of tube nearest RHS 145C, remaining distal tube portion nearest RHS 85B.

*Abaxial.*—Limb between RHS N82C and RHS N82D, proximal 1.0 mm of tube nearest RHS 145B, next proximal 2.0 mm nearest RHS 150D, remaining distal tube portion nearest RHS 86D.

*Androecium.*—Typically five.

Filaments: Typically five, adnate to inner corolla to various heights about 8.0 mm to 13.5 mm from base; free in the distal 1.0 mm to 2.0 mm long and 0.2 mm in diameter; color nearest RHS NN155D;

Anther: Five; oblong elliptic; dorsifixed; oblong, about 2.0 mm long by 0.7 mm wide; color nearest RHS 17A;

Pollen: Nearly microscopic; color nearest RHS 23A;

Gynoecium: One pistil per flower; 12.0 mm long;

Style: Cylindrical; about 9.0 mm long and 0.3 mm diameter when flower is mature; persistent after flower abscission; color nearest RHS 1D;

Stigma: Trifid in proximal 1.5 mm long, about 0.3 mm diameter; color nearest RHS 4C;

Ovary: Inferior; conical; glabrous; acute apex and truncate base; about 1.5 mm long and 1.0 mm diameter; color nearest RHS 143A;

Calyx: Campanulate; pubescent abaxial, glabrous adaxial; about 10.0 mm long and 3.5 mm across at apex;

Sepals: Five; lanceolate; glabrous adaxial and puberulent abaxial; narrowly acute apex, fused in basal 5.0 mm; margin entire; matte abaxial, and lustrous adaxial; individually about 10.0 mm long and 1.0 mm wide at fusion;

Sepal color: Adaxial nearest RHS 137B, fused margins nearest RHS 196D; abaxial nearest RHS 147B with light blush in high light exposure of nearest RHS N187A;

Peduncle: Glabrous; strong, flexible; mostly upright; cylindrical; to about 1.5 mm diameter at base and 2.5 cm long;

Peduncle color: Low light or ventrally nearest RHS 146C; high light or ventrally nearest RHS 146C;

Pedicle: Cylindrical; glabrous; flexible; upright to outwardly; variable lengths from about 8.0 mm to 13.0 mm long and 0.7 mm diameter;

Pedicle color: Variable depending on light exposure; with low light or ventrally nearest RHS N148D; high light or dorsally nearest RHS 146C with strongly maculate nearest RHS 187A;

Fruit and seeds: Not observed;

Hardiness and culture: The new plant grows best with full sun, light moisture and deep drainage; hardy to at least from USDA zone 4 through 8.

Disease and pest resistance: *Phlox* 'Crater Lake' demonstrates excellent powdery mildew resistance under conditions that would normally show symptoms.

I claim:

1. A new and distinct cultivar of Hybrid Creeping *Phlox, Phlox* plant named 'Crater Lake', as herein described and illustrated.

* * * * *